United States Patent [19]

Bak et al.

[11] Patent Number: Plant 7,471

[45] Date of Patent: Mar. 12, 1991

[54] GUZMANIA PLANT NAMED RANA

[75] Inventors: Gerardus J. Bak, AA Assendelft; Nicolaas D. Steur, JL Oude Niedorp; Elly Bak, AA Assendelft, all of Netherlands

[73] Assignee: Corn. Bak B.V., Netherlands

[21] Appl. No.: 360,011

[22] Filed: Jun. 1, 1989

[51] Int. Cl.[5] ..... A01H 5/00

[52] U.S. Cl. ..... Plt./89

[58] Field of Search ..... Plt./88, 89

*Primary Examiner*—Howard J. Locker

*Attorney, Agent, or Firm*—Foley & Lardner, Schwartz, Jeffery, Schwaab, Mack, Blumenthal & Evans

[57] ABSTRACT

A new cultivar of Guzmania named 'Rana' characterized by brilliant red inflorescence, produced on a strong, solid, compact, broad-leafed plant.

2 Drawing Sheets

The present invention relates to a new and distinct cultivar of the genus Guzmania, within the family Bromeliaceae, hereinafter referred to by the cultivar name 'Rana'.

Guzmania comprise a genus of over 100 species of evergreen perennials suitable for cultivation in the home or under glass. Guzmania are predominantly epiphytic with a few terrestrial species and are native to the tropics. For the most part the species vary in diameter from 7 or 8 inches to 3 or 4 feet and have rosettes of glossy, smooth edged leaves.

Floral bracts of Guzmania frequently have brilliant colors and may last for many months. The range of colors for Guzmania is generally from yellow through orange but may also include flame red and red-purple. White or yellow, tubular, three petalled flowers may also appear on a stem or within the leaf rosette but are usually short lived.

Guzmania may be advantageously grown as pot plants for greenhouse or home use. Desirably the plants are shaded from direct sunlight and during the spring to autumn period, the central vase-like part of the leaf rosette is desirably filled with water.

Guzmania is native to tropical America. Leaves of the Guzmania are usually formed as basal rosettes which are stiff and entire and in several vertical ranks. Guzmania have terminal spikes or panicles which are often bracted with petals united in a tube about as long as the calyx. The ovary is superior and the seeds plumose.

Asexual propagation of Guzmania is frequently done through the use of tissue culture practices. Propagation can also be from off-shoots produced by the plant which may then be rooted. The resulting plantlets are detached from the mother plant and may be potted up in a suitable growing mixture.

The new cultivar 'Rana' is a product of a planned breeding program and was originated by the inventors from a cross made during such a program in Assendelft, The Netherlands, in 1983. The male, or pollen parent was a selection from *Guzmania lingulata* identified by Code No. 8320112, and the female, or seed parent was a selection from *Guzmania wittmackii* identified by Code No. 8320126. Both parents have a degree of homozygosity such that the progeny of the cross were and continue to be surprisingly uniform. The selection comprising the new variety was chosen after commencement of flowering of the progeny in 1986, and subsequent and continuous asexual propagation of offshoots has demonstrated that the combination of characteristics as herein disclosed for the new cultivar 'Rana' are firmly fixed and are retained through successive generations of asexual reproduction.

'Rana' is particularly characterized by the following:

1. Its solid, compact growth habit.
2. Relatively wide leaves.
3. Superior floral bract production.
4. Large inflorescence.
5. Its long lasting habit.

Perhaps the closest comparison cultivar is 'Grand Prix'. The above noted characteristics of 'Rana' also serve to distinguish 'Rana' from 'Grand Prix'.

'Rana' has not been tested under all available environmental conditions and the phenotype may vary with variations in environmental conditions such as temperature, light intensity, day length and humidity.

The accompanying color photographic drawings show typical characteristics of 'Rana', with colors being as true as possible with illustrations of this type.

Sheet 1 comprises a perspective view of a full plant with floral bracts.

Sheet 2 contains at the top a somewhat more enlarged showing of the floral bracts and inflorescence, and at the bottom there appears an even more enlarged color showing of the floral bracts and inflorescence.

In the following description, color references are made to The Royal Horticultural Society Color Chart (RHS).

The following traits have been repeatedly observed and in combination distinguish 'Rana' as a new and distinct cultivar. These observations, measurements and descriptions have been performed under greenhouse conditions in Assendelft, The Netherlands.

I. Plant:

*Form.*—Funnel form rosette.

*Height.*—Approximately 50 cm high when flowering.

*Growth habit.*—Stemless.

II. Foliage:

*Size of leaf.*—Approximately 35–45 cm long.

*Shape of leaf.*—Linear — lanceolate.

*Surface texture.*—Smooth.

*Variegation.*—None.

*Color.*—Upperside, near RHS 139A. Underside, near RHS 137B.

III. Bracts:

*Length.*—Primary bracts approximately 12 cm, scape bracts approximately 20 cm.

*Width.*—At the base, approximately 4½ cm.

*General shape.*—Lanceolate.

*Number.*—Approximately 11 primary bracts.

*Texture.*—Smooth.

*Margin.*—Entire.

*Color.*—Inner and outer surfaces, RHS 44A with dark anthocyanous tip.

IV. Flowers:

*Borne.*—Erect stalks.

*Shape of inflorescence.*—Densely bipinnate.

*Size of inflorescence.*—Approximately 25 cm.

*Individual petals.*—(1) Length: For about ¾ of their length, the 3 petals are grown together to form a tube and are approximately 5½ cm long, of which 5 cm is disposed within the floral bracts hidden behind the primary bracts. (2) Width: 6 mm. (3) Quantity: Approximately 80 flowers divided over approximately 11 branches depending on the size of plant and inflorescence. (4) Color: 11B-12C (color appears lighter in photographs).

*Time of blooming.*—In a fully grown plant, flowers start 15 weeks after induction, and at any time of the year.

*Duration of blooms.*—Each flower blooms 1 day and the total duration of blooming is about 6 weeks.

V. Reproductive organs:

*Ovaries.*—Superior.

*Stamens.*—6 in number.

VI. Seed characteristics: Sterile hybrid, therefore no seed.

I claim:

1. A plant of a new and distinct cultivar of Guzmania plant named 'Rana', as illustrated and described.

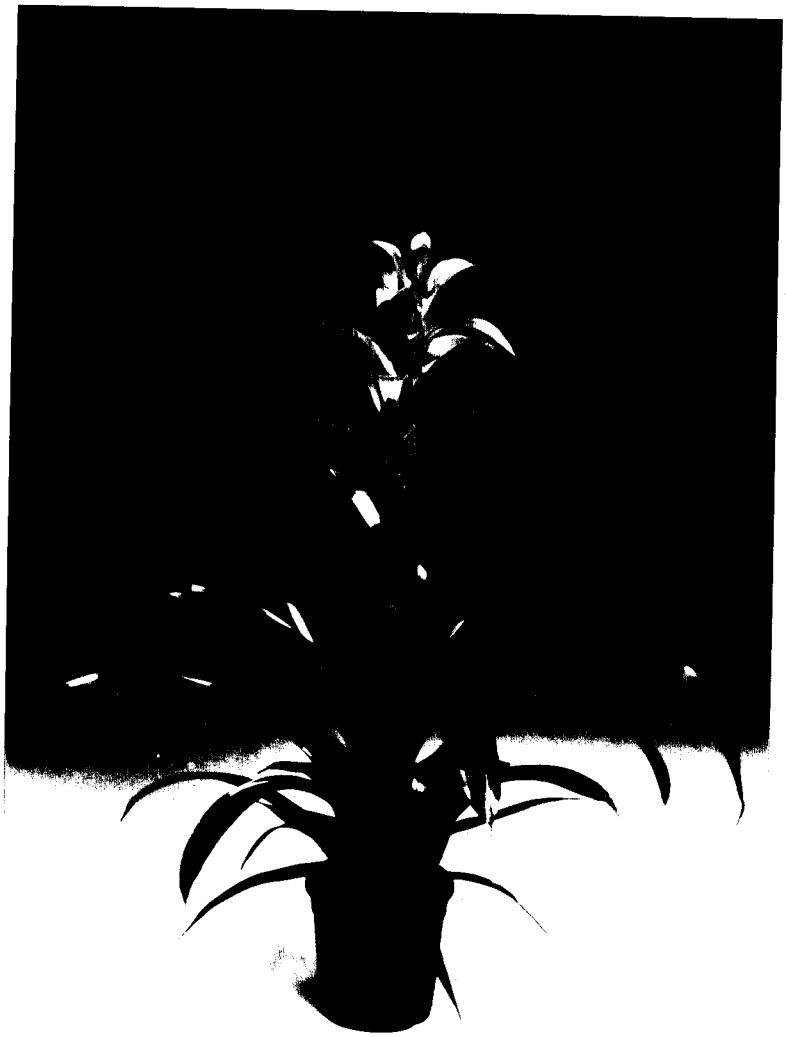

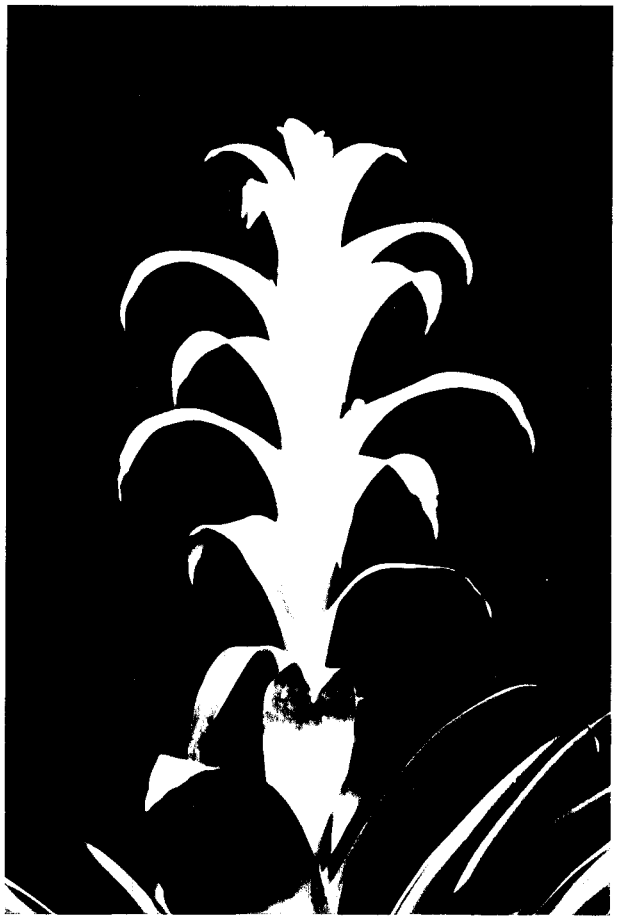
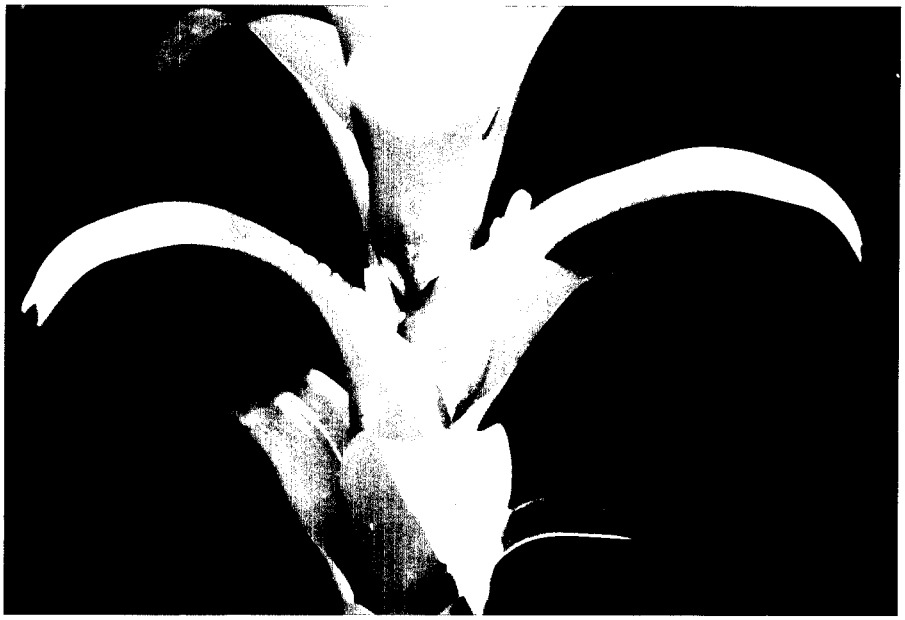

* * * * *